United States Patent [19]

Fujiwara

[11] Patent Number: 4,831,264

[45] Date of Patent: May 16, 1989

[54] METHOD FOR MEASURING THE CONCENTRATION OF ADHESIVE ON A COATING LAYER SURFACE

[75] Inventor: Hideki Fujiwara, Tokyo, Japan

[73] Assignee: Jujo Paper Co., Ltd., Tokyo, Japan

[21] Appl. No.: 80,079

[22] Filed: Jul. 31, 1987

[30] Foreign Application Priority Data

Aug. 4, 1986 [JP] Japan .................................. 61-183067
Jul. 7, 1987 [JP] Japan .................................. 62-169506

[51] Int. Cl.$^4$ ............................................. G01N 21/33
[52] U.S. Cl. .................................... 250/372; 250/359.1
[58] Field of Search ................... 250/372, 358.1, 359.1

[56] References Cited

U.S. PATENT DOCUMENTS 3,325,649  6/1967  Bird ....................................... 250/372
3,395,278  7/1968  McDivitt ............................. 250/372
4,542,296  9/1985  Kleinnibhelink et al. .......... 250/372

OTHER PUBLICATIONS

Kline, "The Use of Ultraviolet Analysis of Coated Paper", 1988, Tapp; Coating Conference.
Fujiwara et al., "Ultraviolet Absorption of Styrene–Butadiene Latex on Pigment–Coated Paper", Tapp; Journal, Dec. 1987, pp. 97–100.

*Primary Examiner*—Carolyn F. Fields
*Attorney, Agent, or Firm*—Oliff & Berridge

[57] ABSTRACT

A method for measuring the concentration of adhesive on the surface of a coating layer which has the steps of irradiating the surface of the coating layer with an ultraviolet ray of the highest peak absorption wavelength of the adhesive, ultraviolet ray of shorter wavelength and ultraviolet ray of longer wavelength, photoelectrically converting the reflected rays and further comparing to calculate them. Thus, this method can be used to measure the concentration of adhesive on the surface of a coating layer and the flat surface distribution of the adhesive by fundamentally measuring with ultraviolet rays. The method is of high reliability despite the presence of gloss or the like.

9 Claims, 6 Drawing Sheets

METHOD FOR MEASURING THE CONCENTRATION OF ADHESIVE ON A COATING LAYER SURFACE

BACKGROUND OF THE INVENTION

The present invention relates to a method for measuring the concentration of an adhesive on the surface of a coating layer coated on a support such as coated paper.

Paper is coated on the surface thereof with various types of pigments to improve its smoothness, brightness, ink receptivity, gloss and opacity. To fabricate such coated paper, adhesives are used to bind pigment particles to each other and to keep the particles on the surface of the base stock. The adhesive typically contains coating slurry together with pigment such as clay or calcium carbonate, and is applied to the surface of the base stock.

When coatings are applied to porous materials such as paper, the adhesive might, however, migrate on the surface of the coating layer or toward the base paper, sometimes into the base paper, a phenomenon known as binder migration, especially during, for example, a drying step. When binder migration occurs, the concentration of adhesive on the surface correspondingly increases, adversely affecting the printability of the paper. For example, binder migration may cause improper inking (print mottle). When the concentration of the adhesive is mottled on the surface of the coating layer, an undesirable effect is produced in that the ink is mottled when offset printing is being conducted. This adverse influence probably occurs because the adhesive itself has no affinity to the printing ink.

In view of the problems discussed above, it is very important to know the concentration of the adhesive on the surface of the coating layer and to know the surface concentration distribution to predict the printability of the coated paper. Thus, the present invention is directed to a technique for accurately measuring the surface concentration of the adhesive and for accurately measuring the surface concentration distribution. Known methods for measuring the concentration of the adhesive on the surface of a coating layer include infrared spectroscopic analysis, analysis with an X-ray microanalyzer and the like.

The infrared spectroscopic analysis is simple but is subject to large errors since the sensitivity of the adhesive is much lower than that of the pigment. The X-ray microanalyzer has, on the other hand, high sensitivity and can measure the distribution of the adhesive on the surface of the coating layer, but necessitates prior treatment with a dye, such as osmium or bromine.

The inventor of the present invention has discovered a correlation between the adhesive concentration on the surface of the coating layer of the coated paper and the ultraviolet ray absorbance and has discovered that styrene-butadiene latex (SB latex) exhibits special absorbance in the ultraviolet ray zone and that the absorbance significantly differs from that of the pigment. The inventor of the present invention has applied the ultraviolet ray absorbance of SB latex to the measurement of the concentration of the adhesive.

However, reflection measurement of light scattered on a sample surface must be employed in the measurement of the concentration of adhesive on the surface of the coating layer. Thus, when light is scattered on the surface of the coating layer because of gloss, the measurement is affected by the scattered light and the concentration of the adhesive cannot be accurately measured.

SUMMARY OF THE INVENTION

Accordingly, an object of the present invention is to provide a method for measuring the concentration of adhesive on the surface of a coating layer and its flat surface concentration distribution by measuring with ultraviolet rays, while compensating for the influence of gloss, to obtain the measured result with high reliability.

In accordance with the present invention, it has been found that the influence of light scattered due to the state of the surface of a coating layer, for example, gloss, is removed by measurement using three wavelengths within absorption. The peak absorption of the adhesive in the coating layer is the center of the quantitative surface concentration measurement.

More particularly, in order to achieve the above and other objects, there is provided according to the present invention a method for measuring the concentration of adhesive on the surface of a coating layer comprising the steps of: (1) irradiating the surface of the coating layer with an ultraviolet ray of the highest peak absorption wavelength of the adhesive, an ultraviolet ray of a shorter wavelength and an ultraviolet ray of longer wavelength, and (2) photoelectrically converting the reflected rays and further comparing to calculate them.

These and other objects and features will become more apparent from the following description of the preferred embodiments of the present invention when read in connection with the accompanying drawings.

DESCRIPTION OF THE PREFERRED EMBODIMENTS

Embodiments for measuring the concentration of adhesive on the surface of coating layers according to the present invention will now be described in detail with reference to the accompanying drawings.

Figure 4:
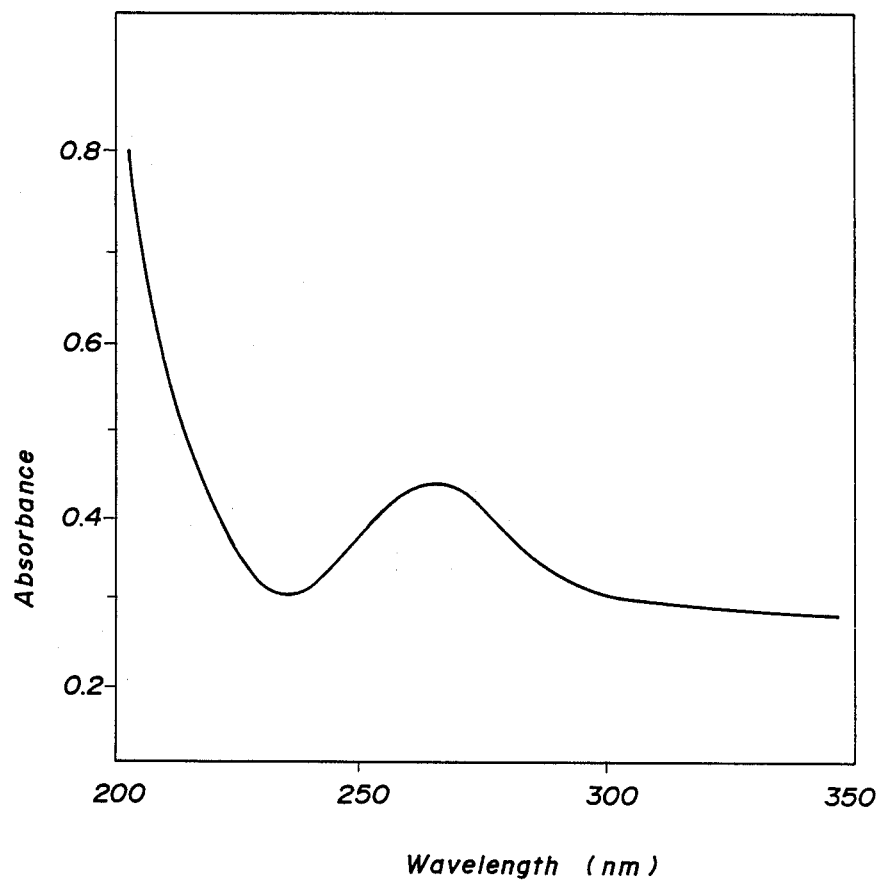
FIG. 4 is a graph showing the ultraviolet absorbance of SB latex.

FIG. 4 is a graph showing the relationship between the wavelength of ultraviolet rays and the absorbance thereof by SB latex. In FIG. 4, the wavelength of ultraviolet rays at which the highest peak of the absorption by the SB latex occurs is about 260 nm. When measuring the concentration of the SB latex, ultraviolet rays of a wavelength near 260 nm are used as the center of the three wavelengths. Similarly, when measuring the concentration of other adhesives, the absorption ultraviolet ray wavelength of the highest peak must be determined to measure the concentration.

Figure 2:
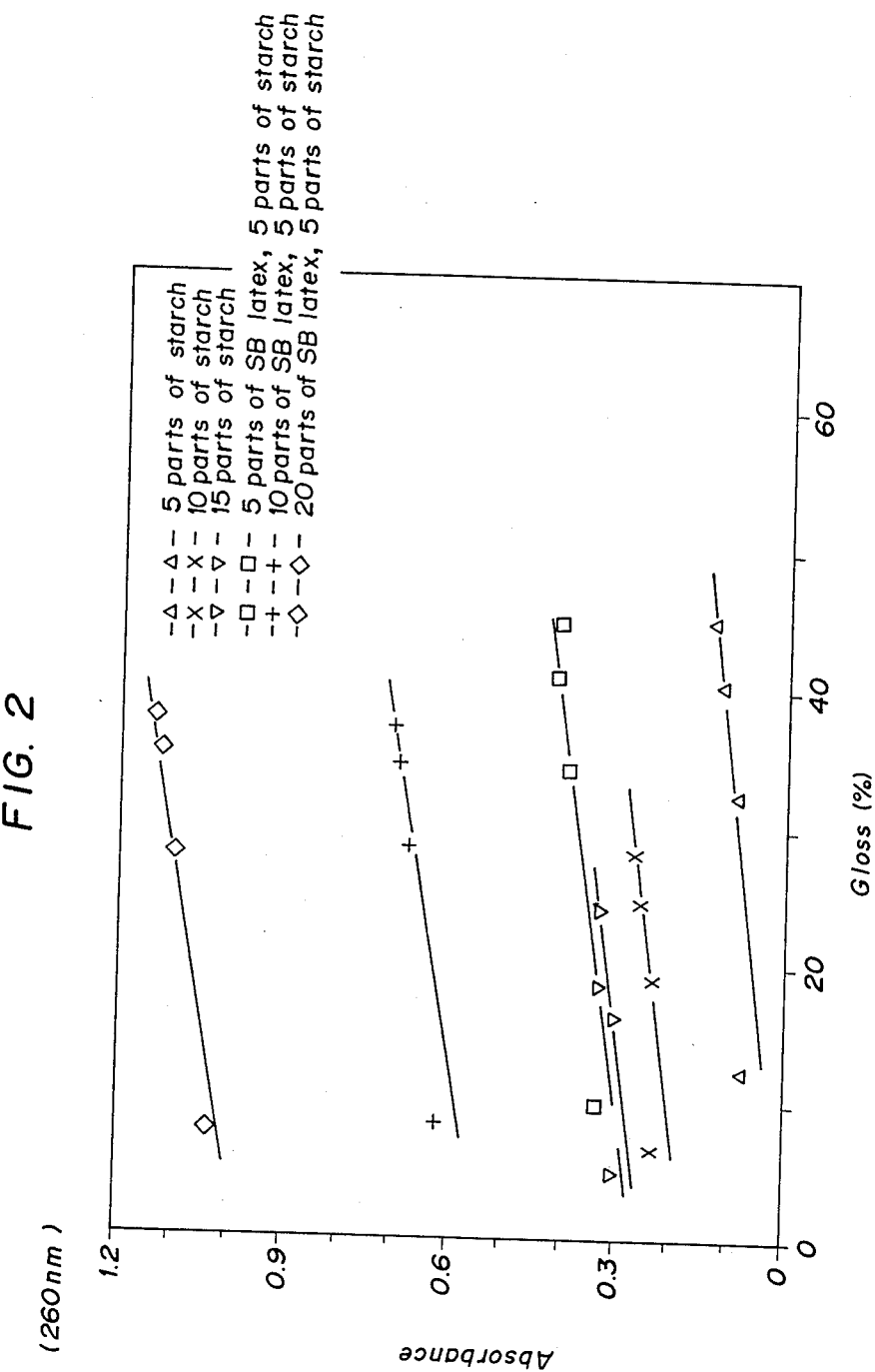
FIG. 2 is a graph showing the relationship between the gloss of the coating layer and the absorbance before correction.

In the method of the present invention, ultraviolet rays of shorter and longer wavelengths are used in addition to ultraviolet rays having the highest peak absorption wavelength. As will be described with reference to FIG. 2, correct quantitative measurement cannot be obtained by analysis using only ultraviolet rays having the highest peak absorption wavelength. FIG. 2 shows the relationship between the gloss and the absorbance of ultraviolet rays having a wavelength of 260 nm by coated paper using three types of solution comprising 5, 10 and 15 parts of starch to 100 parts of calcium carbonate pigment and three types of solution comprising 5 parts of starch and 5, 10 and 20 parts of SB latex. The absorbance of light of wavelength equal to 260 nm is affected by the gloss of the surface of coated paper, and is also affected by the presence of the starch which does not absorb the ultraviolet ray. Therefore, the correct quantitative result cannot be obtained by measurement with light of only one wavelength. The reason that the increase in the starch increases the absorbance is not always apparent, but it is possible that the absorbance is increased due to a variation in the scattering state of the light on the surface of the coating layer as a result of the presence of the starch.

Figure 6:
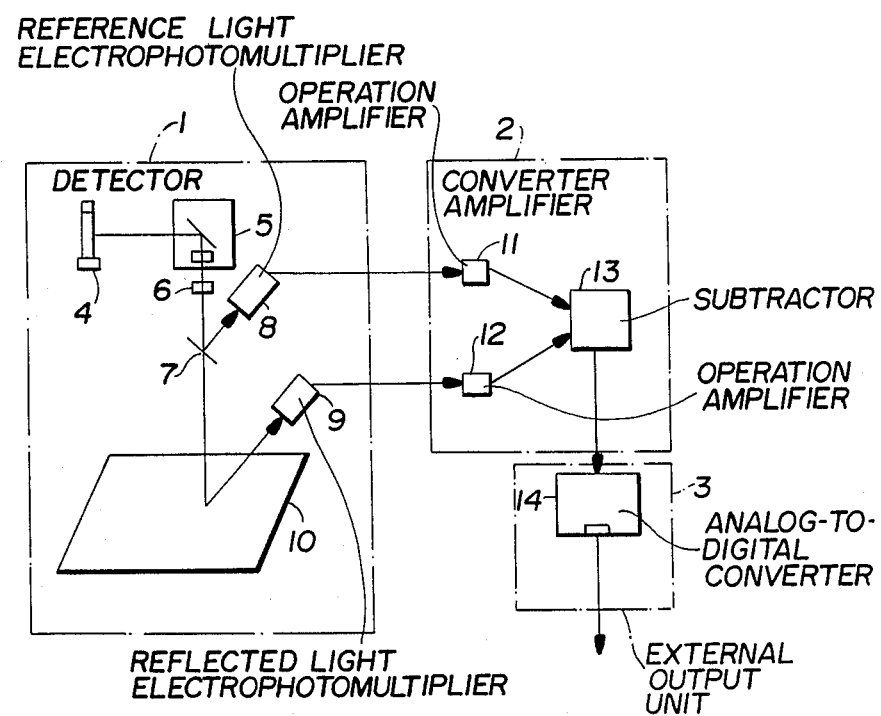
FIG. 6 is an explanatory view showing an example of the construction of an apparatus for measuring in accordance with the present invention.

An embodiment of an apparatus for measuring the concentration of the adhesive on the surface of a coating layer according to the present invention is shown in FIG. 6. This apparatus comprises a detector 1, a converter amplifier 2, and an external output unit 3 as main components. The detector has deuterium lamp 4, a filter 5, a diaphragm 6, a half mirror 7, a reference light electrophotomultiplier 8, a reflected light electrophotomultiplier 9 and a sample base 10.

To measure the concentration of adhesive on a coating layer, the ultraviolet ray irradiated from the deuterium lamp 4 passes through the filter 5 after which it is monochromatic light of specific wavelength. The monochromic light is focused by the diaphragm 6 into a spot light and is then spectrally analyzed by the half mirror 7. A portion of the light is photometered as a reference light by the reference light electrophotomultiplier 8, and another portion of the light is reflected on the sample being analyzed, which sample is mounted on the sample base 10. Part of the reflected light is photometered by the reflected light electrophotomultiplier 9. The light is converted by the electrophotomultiplier into a current, and the resultant current is then converted into voltages $E_1$ and $E_2$ by operation amplifiers 11, 12 of the converter amplifier 2. The voltages E1, E2 are subtracted by a subtractor 13, and are converted by an analog-to-digital converter 14 of the external output unit 3 into a digital signal. The digital signal is transferred to a data processor such as a computer or a recorder.

In accordance with the present invention, the measured result is not affected by the influence of other physical properties such as gloss and can be quantitatively obtained by calculating and comparing the optical densities of the three wavelengths. The removal of the influence of gloss will be described in detail.

Figure 3:
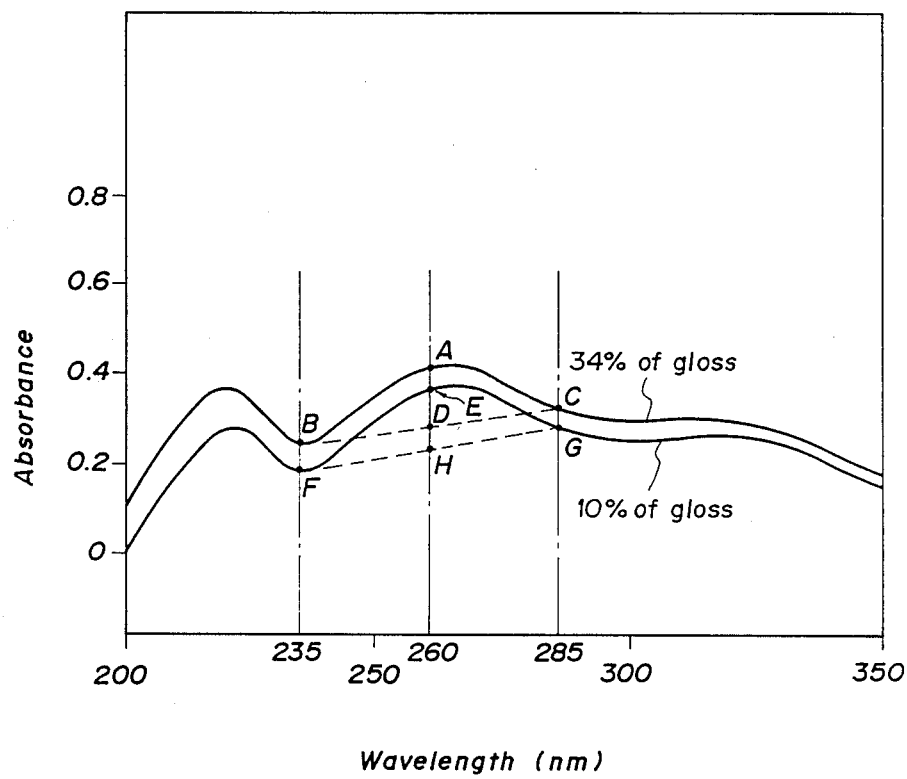
FIG. 3 is a graph showing the relationship between the wavelength of the ultraviolet ray for the gloss and the absorbance.

FIG. 3 shows measurement of the absorbance of ultraviolet ray (of wavelengths from 200 to 350 nm) prepared with 10% and 34% of gloss. The difference in gloss is obtained by applying different degrees of supercalendering coated paper with solution comprising 5 parts of starch and 5 parts of SB latex in 100 parts of calcium carbonate of coated paper such as that used in formulating the graph shown in FIG. 2. Referring to FIG. 3, the apparent absorbance of light of any wavelength is greater when the gloss of the coated paper is 34% as opposed to 10%.

When the curves of both the absorption spectra of 34% and 10% of gloss are designated by f(x) and g(x), the relationship between both the curves can be substantially represented by the equation $f(x)-g(x)=ax+b$. Base lines BC and FG were drawn using the measured values at wavelengths of 235 nm and 285 nm as the end points. These are the shorter and longer wavelengths, discussed above, relative to the highest peak absorption wavelength (260 nm) of SB latex. The differences of the points D and H on the base lines in the wavelength of 260 nm and the measured values A and E of the wavelength of 260 nm, respectively, are denoted AD and EH. If the relationship between the curves of both the spectra is represented by the equation $f(x)-g(x)=ax+b$, AD and EH are equal. Thus, by calculation according to this relationship, the influence of the gloss can be compensated for. Even when the relationship between the curves of the spectra differs slightly from the equation $f(x)-g(x)=ax+b$, AD is nearly equal to EH, and the influence of the gloss can be substantially compensated for, The equation for producing the base line will be described.

The absorbance at corrected 260 nm = $S_{260} - ((S_{285}-S_{235})/2 + S_{235})$ where $S_{260}$, $S_{235}$, $S_{285}$ represent the apparent absorbance measured at wavelengths of 260, 235 and 285 nm, respectively.

In the present invention, the ultraviolet rays of shorter and longer wavelength, relative to the highest peak absorption wavelength may be somewhat arbitrarily set. In FIG. 3, the reason that 235 and 285 nm are selected is because of the convenience of calculations and the exclusion of the measuring error. More specifically, since the shorter and longer wavelenths each differ from the highest peak absorption wavelength by 25 nm, FG/FH=2, thereby simplifying calculation.

In general, as shown in FIG. 3, $FG/FH=(L-S)/(P-S)$, where L=the wavelength of the ultraviolet ray of longer wavelength, P=the wavelength of the ultraviolet ray of the highest peak absorption, and S=the wavelength of the ultraviolet ray of shorter wavelength.

Thus, the complete equation for the calculation of corrected absorbance is:

$$S_c = S_p - ((S_1 - S_s)/(L-S)/(P-S)) + S_s),$$

wherein:

$S_c$ is the corrected abosrbance, $S_p$ is the absorbance of the ulraviolet ray of the highest peak absorption wavelength, $S_s$ is the absorbance of the ultraviolet ray of shorter wavelength, and $S_1$ is the absorbance of the ultraviolet ray of longer wavelength.

As discussed above, when L and S differ from P by equal amounts, $(L-S)/(P-S)=2$, and the equation simplifies to $S_c = S_p - ((S_1-S_s)/2 + S_s)$. Since 235 nm is not very far from the highest peak and is situated at a minimum peak, the measuring error can be effectively compensated for.

Figure 1:
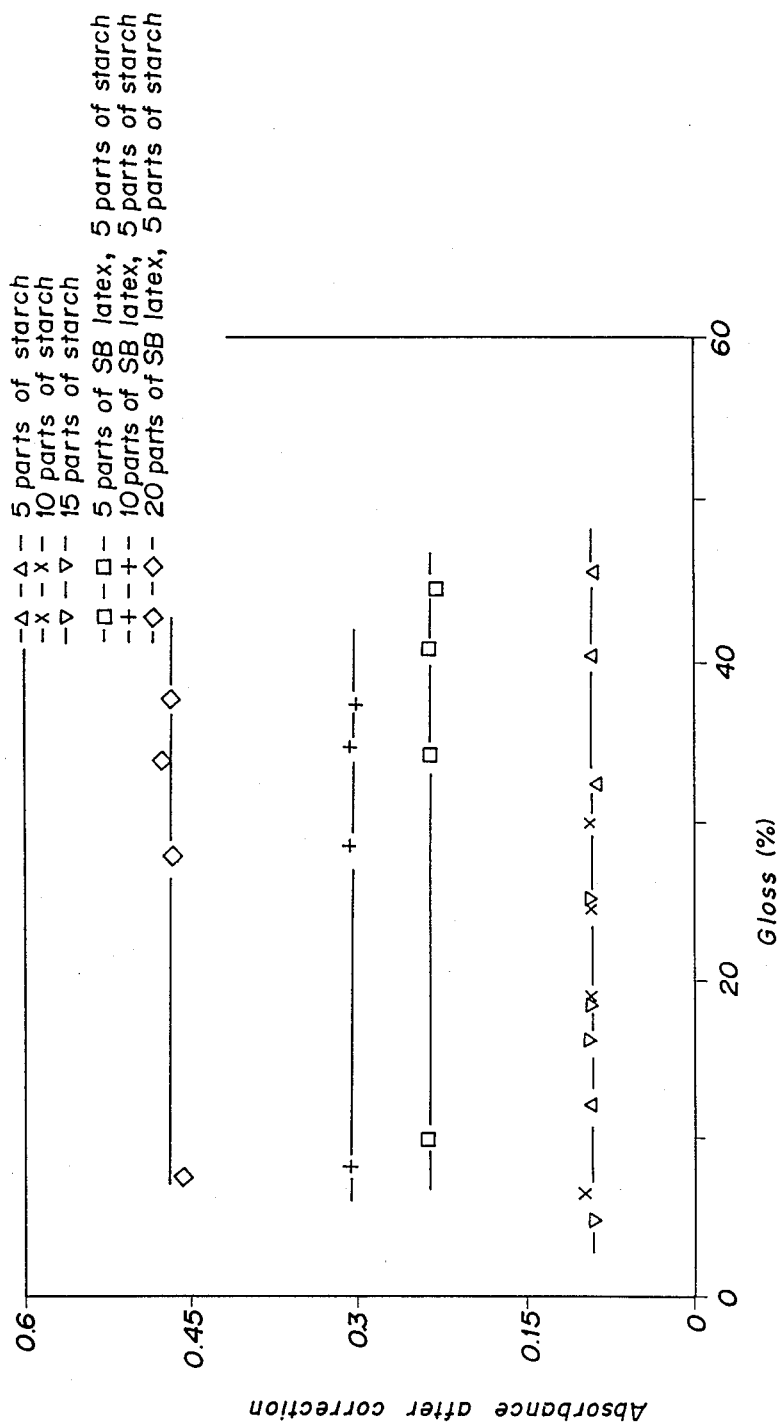
FIG. 1 is a graph showing the relationship between the gloss of the coating layer and absorbance corrected according to the present invention.

As described above, when the graph in FIG. 2 is corrected as described above, a graph such as the one shown in FIG. 1 is obtained. FIG. 1 therefore shows the influence of the starch with the influence of the gloss of the sample having been compensated for. The influence of the presence of starch in the absence of gloss is apparent from the fact that the plots for samples containing starch in amounts of 5, 10 and 15 parts fall on approximately the same line in FIG. 1.

Figure 5:
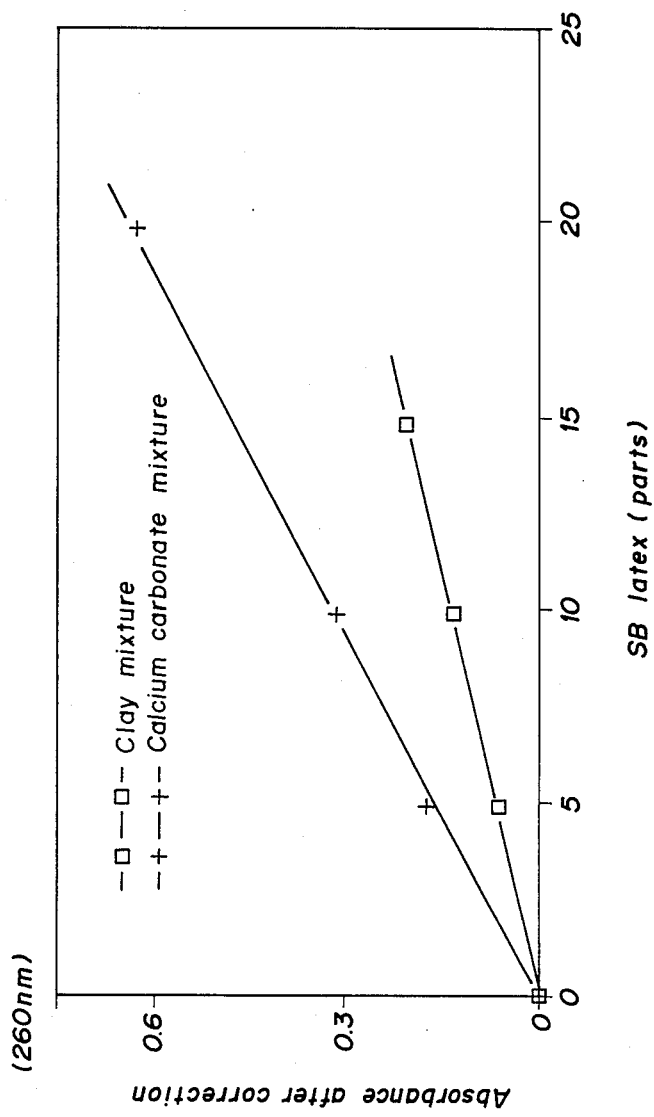
FIG. 5 is a graph showing the relationship between the adhesive concentration of the coating layer and the corrected absorbance.

FIG. 5 shows a graph of the measurement of the surface of coated paper fabricated with an adhesive solution containing 60 percent by weight of adhesive mixed with 5, 10, 15 or 20 parts of SB latex to 100 parts of clay or calcium carbonate pigment. The amount of adhesive in the sample was 10 g/m2 (dry weight), and only one side was coated with adhesive. The concentration of the SB latex is shown to be proportional to the absorbance after the correction in accordance with the present invention. The slopes of the lines differ depending upon the type of pigment because of the differences in the shapes and sizes of the pigments. These measured values are obtained by superposing the sample, lining a glass plate of ultraviolet ray absorption substance on the sample, and lining a silica gel plate exhibiting no absorption. In all cases, the measured values were the same, because the scattered light on the surface of the coating layer is detected.

The measurement of the distribution of adhesive on the surface of the coating layer will now be described. To effect this measurement, an apparatus capable of moving laterally and longitudinally relatively between the sample and the ultraviolet rays is provided. For example, in the apparatus shown in FIG. 6, the sample base 10 is moved laterally and longitudinally at predetermined intervals using an XY stage having a stepping motor for the sample base 10.

The distributed state of the adhesive may be measured by the following procedure using an apparatus constructed as described above. Samples of coated paper coated with adhesive solution of 60% of solid concentration mixed with 100 parts of clay, 10 parts of SB latex containing 10 g/m2 (dry weight) of adhesive on the surface of base paper, were dried by natural drying at room temperature and by hot blast drying. The samples were irradiated with fine ultraviolet light spots having three wavelengths, namely, 235, 260 and 285 nm longitudinally at 4 mm intervals, 60 mm long and laterally at 1 mm intervals, 63 mm long. The size of each sample was 0.4 mm×0.4 mm.

The average absorbance after correction of the samples formed by natural drying was 0.326, and its standard deviation was 0.004. The average absorbance after correction of the samples formed by hot blast drying was 0.432, and its standard deviation ws 0.006. These measured results indicate that the SB latex moves onto the surface of the coating layer due to the abrupt hot blast drying and its distribution is irregular as compared with that of the natural drying. The result conforms to the empirical fact that the printability of coated paper decreases when abrupt hot blast drying is executed. As described above, according to the method of the present invention, the surface concentration distribution of the adhesive on the coating layer can be measured.

A method of irradiating with an ultraviolet ray of a specific wavelength will be further described. The longitudinal and lateral size of the fine ultraviolet ray spot is suitably from 0.01 to 2 mm. When the adhesive distribution on the surface of the coating layer is measured, the sample base and the spot are continuously moved laterally and longitudinally relative to one another. The size of the spot is determined by considering the area and the measuring interval of the samples. For example, when a 50 cm2 sample is measured at an interval of 2 mm longitudinally and laterally, satisfactory results can be obtained by using a spot measuring 0.5 mm laterally and longitudinally.

According to the present invention as described above, the adhesive concentration and the distribution can be accurately and rapidly measured despite any influence of scattered light on the irregular surface of the coating layer and without the necessity of pretreatment. In accordance with the present invention, irradiating light of the highest peak absorption wavelength as well as irradiating light having shorter and longer wavelengths are used to make the measurements of the coating layer being analyzed. This measuring method is not limited to any particular type of paper. That is, coated layers can be analyzed irrespective of the nature of the support, for example, coated synthetic resin, metal or glass layers can be analyzed.

What is claimed is:

1. A method for measuring the concentration of adhesive on the surface of a pigment coating layer coated on a support comprising the steps of:

irradiating the surface of the coating layer with an ultraviolet ray of the highest peak absorption wavelength of the adhesive, an ultraviolet ray of shorter wavelength and an ultraviolet ray of longer wavelength, and photoelectrically determining the absorbance of each of said rays by the surface of the pigment coating layer and calculating a corrected absorbance from which the concentration of adhesive can be determined.

2. The method according to claim 1, wherein said pigment coating layer adhesive comprises a stryrene-butadiene latex, the highest peak absorption wavelength is 260 nm and the shorter wavelength is 235 nm.

3. The method according to claim 2, wherein the longer wavelength is 285 nm.

4. The method according to claim 1, wherein said support is paper.

5. The method according to claim 1, wherein said support is selected from the group consisting of synthetic resin, metal and glass.

6. The method according to claim 1, wherein the irradiating spot of the ultraviolet ray measures from 0.01 mm to 2 mm laterally and longitudinally.

7. The method according to claim 1, wherein the pigment concentration of adhesive in the coating layer surface is measured by scanning the irradiating spot of the ultraviolet ray on the pigment coating layer surface.

8. A method for measuring the concentration of adhesive on the surface of a pigment coating layer comprising the steps of:

irradiating the surface of the pigment coating layer with an ultraviolet ray of the highest peak absorption wavelength of the adhesive, an ultraviolet ray of shorter wavelength and an ultraviolet ray of longer wavelength to obtain the absorbance of the ultraviolet ray of each wavelength.

obtaining a corrected absorbance ($S_C$) of the ultraviolet ray of the highest peak absorption wavelength from the following equation:

$$S_C = S_p - ((S_L - S_S)/2 + S_S)$$

where $S_C$ is the corrected absorbance,
$S_p$ is the absorbance of the ultraviolet ray of the highest peak absorption wavelength,
$S_S$ is the absorbance of the ultraviolet ray of shorter wavelength,
$S_L$ is the absorbance of the ultraviolet ray of longer wavelength, and
comparing the corrected absorbance with previously determined values for corrected absorbance correlated with pigment coating layer adhesive concentrations to determine the concentration of the adhesive.

9. A method for measuring the concentration of adhesive on the surface of a pigment coating layer comprising the steps of:
irradiating the surface of the pigment coating layer with an ultraviolet ray of the highest peak absorption wavelength (P) of the adhesive, an ultraviolet ray of shorter wavelength (S) and an ultraviolet ray of longer wavelength (L) to obtain the absorbance of the ultraviolet ray of each wavelength,
obtaining a corrected absorbance ($S_C$) of the ultraviolet ray of the highest peak absorption wavelength from the following equation:

$$S_C = S_p - ((S_L - S_S)/(L-S)/(P-S)) + S_S$$

where
$S_C$ is the corrected absorbance,
$S_p$ is the absorbance of the ultraviolet ray of the highest peak absorption wavelength,
$S_S$ is the absorbance of the ultraviolet ray of shorter wavelength,
$S_L$ is the absorbance of the ultraviolet ray of longer wavelength, and
comparing the corrected absorbance with previously determined values for corrected absorbance correlated with pigment coating layer adhesive concentrations to determine the concentration of the adhesive.

* * * * *